(12) United States Patent
Nakashima

(10) Patent No.: US 11,471,230 B2
(45) Date of Patent: Oct. 18, 2022

(54) MEDICAL SYSTEM AND MEDICAL SYSTEM OPERATION METHOD

(71) Applicant: OLYMPUS CORPORATION, Tokyo (JP)

(72) Inventor: Kohei Nakashima, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 552 days.

(21) Appl. No.: 16/701,311

(22) Filed: Dec. 3, 2019

(65) Prior Publication Data

US 2020/0100857 A1  Apr. 2, 2020

Related U.S. Application Data

(63) Continuation of application No. PCT/JP2017/020784, filed on Jun. 5, 2017.

(51) Int. Cl.
*A61B 34/00* (2016.01)
*A61B 34/37* (2016.01)
(Continued)

(52) U.S. Cl.
CPC .............. *A61B 34/37* (2016.02); *B25J 3/04* (2013.01); *B25J 9/161* (2013.01); *B25J 13/065* (2013.01); *B25J 15/0052* (2013.01); *A61B 17/29* (2013.01); *A61B 17/320016* (2013.01); *A61B 2017/00199* (2013.01); *A61B 2034/303* (2016.02); *A61B 2034/742* (2016.02)

(58) Field of Classification Search
CPC . B25J 3/04; B25J 15/0052; B25J 9/161; B25J 13/065; A61B 34/37; A61B 2017/00199

USPC ......... 600/1, 300; 606/1; 702/188; 901/4, 41
See application file for complete search history.

(56) References Cited

U.S. PATENT DOCUMENTS 11,116,534 B2 * 9/2021 Kapadia ................. A61B 34/71
2004/0240981 A1 * 12/2004 Dothan .................. B65G 61/00
414/795.4

(Continued)

FOREIGN PATENT DOCUMENTS

JP  2003-265500 A  9/2003
JP  2004-129782 A  4/2004
(Continued)

OTHER PUBLICATIONS

International Search Report dated Sep. 5, 2017 received in PCT/JP2017/020784.

*Primary Examiner* — Dalena Tran
(74) *Attorney, Agent, or Firm* — Scully, Scott, Murphy & Presser, P.C.

(57) ABSTRACT

A medical system includes: a slave having at least one moving part; an operation device having at least one operation part; and a processor that controls operations of the slave based on a conversion table that associates operations of the moving part of the slave with inputs of the operation part of the operation device. The processor is programmed to execute: acquiring user identification information of a user of the slave, slave identification information of the slave, and operation device identification information of the operation device, and generating and proposing the conversion table based on the user identification information, the slave identification information, and the operation device identification information.

13 Claims, 15 Drawing Sheets

(51) Int. Cl.
*B25J 3/04* (2006.01)
*B25J 9/16* (2006.01)
*B25J 13/06* (2006.01)
*B25J 15/00* (2006.01)
*A61B 34/30* (2016.01)
*A61B 17/29* (2006.01)
*A61B 17/32* (2006.01)
*A61B 17/00* (2006.01)

(56) References Cited

U.S. PATENT DOCUMENTS

| | | | |
|---|---|---|---|
| 2009/0254109 A1 | 10/2009 | Sekino et al. | |
| 2011/0218677 A1* | 9/2011 | Jinno | B25J 13/00 |
| | | | 901/31 |
| 2013/0078624 A1* | 3/2013 | Holmes | G01N 35/00 |
| | | | 73/61.52 |
| 2013/0079599 A1* | 3/2013 | Holmes | A61B 8/483 |
| | | | 600/300 |
| 2021/0369374 A1* | 12/2021 | Simi | B25J 9/0009 |

FOREIGN PATENT DOCUMENTS

| | | |
|---|---|---|
| JP | 2009-247434 A | 10/2009 |
| JP | 2012-213426 A | 11/2012 |
| JP | 2016-002280 A | 1/2016 |
| WO | 2014/104088 A1 | 7/2014 |
| WO | 2016194539 A1 | 12/2016 |

\* cited by examiner

J3 : RIGHT / LEFT
+ : RIGHT
− : LEFT

J2 : UP/DOWN
+ : UP
− : DOWN

J1 : ROTATION
+ : CW
− : CCW

| UserA | | S01 | | |
|---|---|---|---|---|
| | | J1 | J2 | J3 |
| M01 | In1a | 1 | 0 | 0 |
| | In1b | -1 | 0 | 0 |
| | In2a | 0 | 1 | 0 |
| | In2b | 0 | -1 | 0 |
| | In3a | 0 | 0 | 1 |
| | In3b | 0 | 0 | -1 |

| UserB | | S01 | | |
|---|---|---|---|---|
| | | J1 | J2 | J3 |
| M01 | In1a | 1 | 0 | 0 |
| | In1b | -1 | 0 | 0 |
| | In2a | 0 | 0 | 1 |
| | In2b | 0 | 0 | -1 |
| | In3a | 0 | 1 | 0 |
| | In3b | 0 | -1 | 0 |

| UserA | | S01 | | |
|---|---|---|---|---|
| | | J1 | J2 | J3 |
| M01 | 1+a | 1 | 0 | 0 |
| | 1+b | -1 | 0 | 0 |
| | 2+a | 0 | 1 | 0 |
| | 2+b | 0 | -1 | 0 |
| | 3+a | 0 | 0 | 1 |
| | 3+b | 0 | 0 | -1 |

MEDICAL SYSTEM AND MEDICAL SYSTEM OPERATION METHOD

CROSS REFERENCE TO RELATED APPLICATIONS

This application is a continuation application based on a PCT Patent Application No. PCT/JP2017/020784, filed on Jun. 5, 2017, the content of which is incorporated herein by reference.

BACKGROUND

Technical Field

The present invention relates to a medical system including a robot arm and an operation method of a medical system including a robot arm.

Background Art

A treatment tool unit having a treating part such as a grasping forceps or an electric knife at a distal end of a robot arm having multiple degrees of freedom is used for medical treatment. An operator needs to control the operation of the treatment tool unit by operating a moving part such as a joint of the robot arm and a treatment tool of the treatment tool unit.

An operation device for the treatment tool unit has a plurality of operation parts in order to operate a plurality of moving parts of the treatment tool unit. The operation of the moving parts of the treatment tool unit is associated with the operation parts of the operation device.

During a medical procedure, an operator may perform treatment by exchanging different types of treatment tool units. Different types of treatment tool units have different configurations, and the types and number of moving parts are different. On the other hand, even when the treatment tool unit is replaced, the same operation device may be used. Therefore, every time the treatment tool unit is replaced, it is essential to associate the moving part of the treatment tool unit with the operation part of the operation device.

In addition, different operators may operate the same treatment tool unit. An operator may customize the association between the moving part of the treatment tool unit and the operation part of the operation device to be easy to use. The association between the moving part of the treatment tool unit and the operation part of the operation device may differ from one operator to another. Therefore, every time the operator changes, it is essential to associate the moving part of the treatment tool unit with the operation part of the operation device.

Japanese Unexamined Patent Application, First Publication No. 2016-002280 describes a medical system that associates a treatment tool unit and an operation device based on correspondence information. When the medical system has correspondence information for performing an association process, the treatment tool unit and the operation device are automatically associated with each other.

SUMMARY

A medical system includes a slave having at least one moving part; an operation device having at least one operation part; and a processor that controls operations of the slave based on a conversion table that associates operations of the moving part of the slave with inputs of the operation part of the operation device. The processor is programmed to execute: acquiring user identification information of a user of the slave, slave identification information of the slave, and operation device identification information of the operation device, and generating and proposing the conversion table based on the user identification information, the slave identification information, and the operation device identification information.

The processor may be programmed to execute: causing a memory to store the conversion table used by the user as a conversion table history together with the user identification information, the slave identification information, and the operation device identification information, when there is the conversion table history corresponding to the user identification information, the slave identification information, and the operation device identification information, proposing the corresponding conversion table history as a conversion table, and when there is no conversion table history corresponding to the user identification information, the slave identification information, and the operation device identification information, generating and proposing the conversion table by referring to the conversion table history.

The processor may be programmed to execute: causing a memory to store an operation history of the operation device operated by the user together with the user identification information, the slave identification information, and the operation device identification information, and generating and proposing the conversion table based on the operation history, so that a deviation in the number of operations in a plurality of operation parts is reduced or a total number of the operations is reduced.

The processor may be programmed to execute: when a period in which there is no operation input to the operation device exceeds a predetermined period, generating and proposing the conversion table again.

The medical system may further include an endoscope, and the processor may be programmed to execute: generating and proposing the conversion table referring to a relative positional relationship between the endoscope and the slave.

The medical system may further include: an endoscope; and a display part configured to display an image captured by the endoscope, and the processor may be programmed to execute: when a period in which there is no operation input to the operation device exceeds a predetermined period, causing the display part to display the image which superimposes an identification display of the operation part corresponding to the moving part of the imaged slave, on a position where the moving part is imaged.

The medical system may further include a display part configured to display an image, and the processor may be programmed to execute: when the conversion table is generated and proposed, causing the display part to display a pseudo image of the slave that operates based on the generated conversion table.

A medical system operation method includes: a conversion table storage process in which a conversion table associating an moving part of a slave with an operation part of an operation device that receives an operation of the slave is stored, together with user identification information of a user of the slave, slave identification information of the slave, and operation device identification information of the operation device, as a conversion table history; and a conversion table proposing process in which the conversion table is generated and proposed with reference to the conversion table history.

The medical system operation method may further include: an operation history storage process in which an operation history of the operation device operated by the user is stored together with the user identification information, the slave identification information, and the operation device identification information. In the conversion table proposing process, the conversion table may be proposed and generated based on the operation history, so that a deviation of the number of operations in a plurality of operation parts is reduced or a total number of the operations is reduced.

In the conversion table proposing process, the conversion table may be generated and proposed again when a period in which there is no operation input to the operation device exceeds a predetermined period.

In the conversion table proposing process, a relative positional relationship between the endoscope and the slave may be referred to, to generate and propose the conversion table.

The medical system operation method may further include: an association display process in which, when a period in which there is no operation input to the operation device exceeds a predetermined period, an identification display of the operation part corresponding to the moving part of the slave imaged by the endoscope is superimposed on a position where the moving part is imaged.

The medical system operation method may further include: an interactive display process in which a pseudo image of the slave that operates based on the generated conversion table is displayed on a display part when the conversion table is generated and proposed.

DETAILED DESCRIPTION OF THE PREFERRED EMBODIMENTS

First Embodiment

A first embodiment of the present invention will be described with reference to FIGS. 1 to 15.

Figure 1:
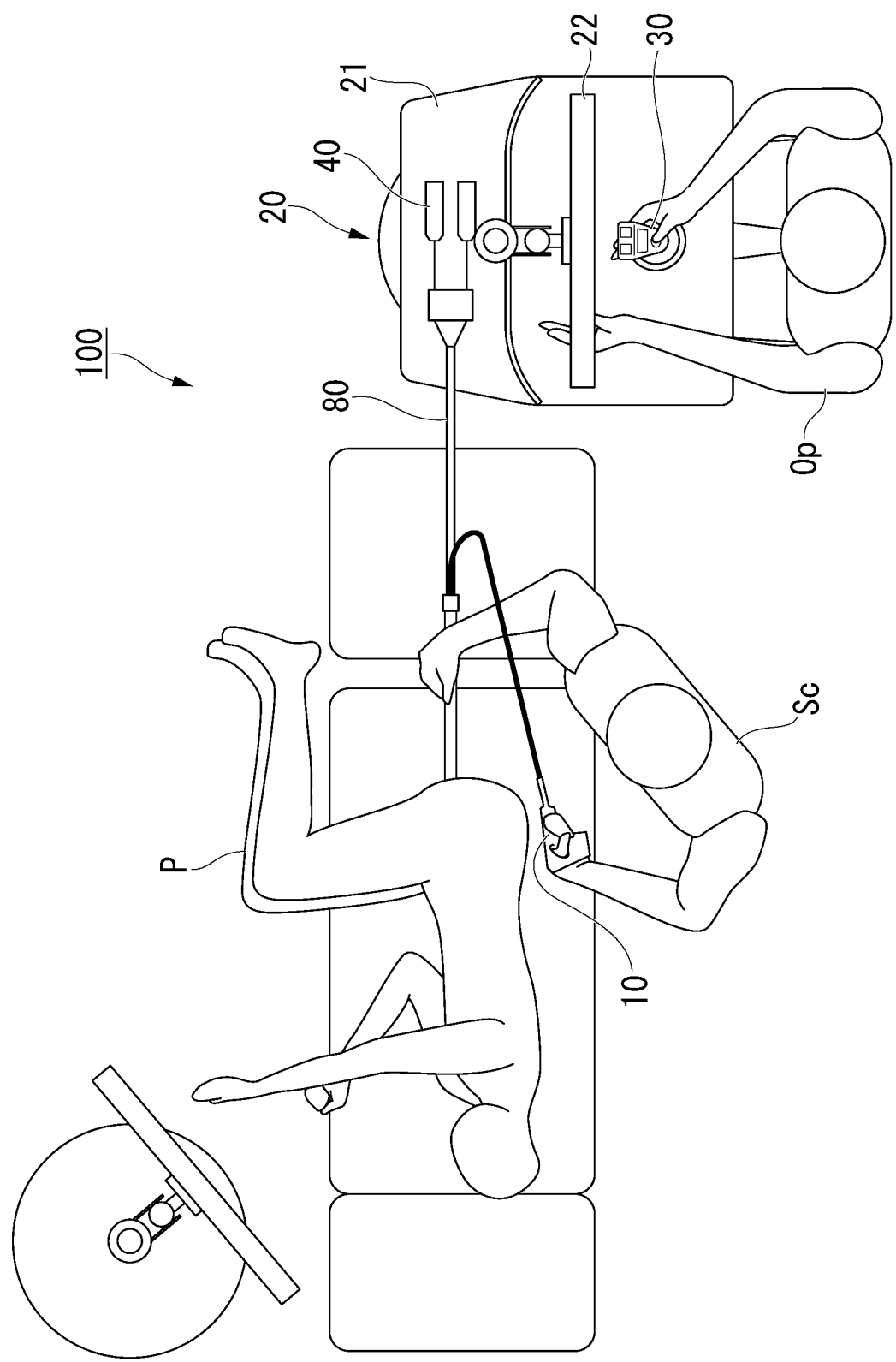
FIG. 1 is a view showing an overall configuration of a medical system according to a first embodiment of the present invention.

FIG. 1 is a view showing an overall configuration of a medical system 100 according to the present embodiment. The medical system 100 includes an endoscope 10 configured to observe the inside of the patient P, a manipulator 20 having a treatment tool unit (slave device) 40 configured to perform treatment inside the patient P, and an overtube 80 through which the endoscope 10 and the manipulator 20 are inserted.

The endoscope 10 is an apparatus for observing the inside of the patient P, and can be appropriately selected from various known configurations in consideration of performance, use, or the like.

Figure 2:
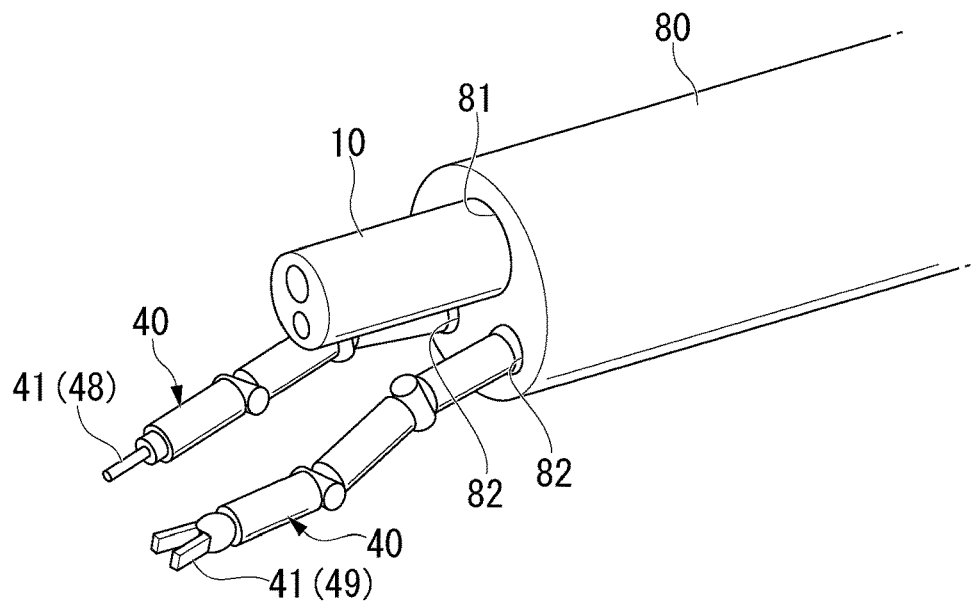
FIG. 2 is a view showing a distal end of an overtube of the medical system.

FIG. 2 is a view showing the configuration of the distal end of the overtube 80.

As shown in FIG. 2, the overtube 80 has a first lumen 81 through which the endoscope 10 is inserted, and a second lumen 82 through which the treatment tool unit 40 is inserted. The overtube 80 can be appropriately selected from various known configurations in consideration of the size or the like. When an overtube having a curved portion on the distal end side is used, it easily reaches the target portion to be treated.

In the two treatment tool units 40 shown in FIG. 2, one is equipped with a grasping forceps 49 as the treating part 41, and the other is equipped with an electric knife 48 as the treating part 41.

The manipulator 20 includes a console 21 (master device) operated by the operator Op, and a treatment tool unit 40 (slave device) mounted on the console 21. The treatment tool unit 40 having a treating part 41 such as the gripping forceps 49 and the electric knife 48 suitable for treatment is selected and mounted on the console 21.

Figure 3:
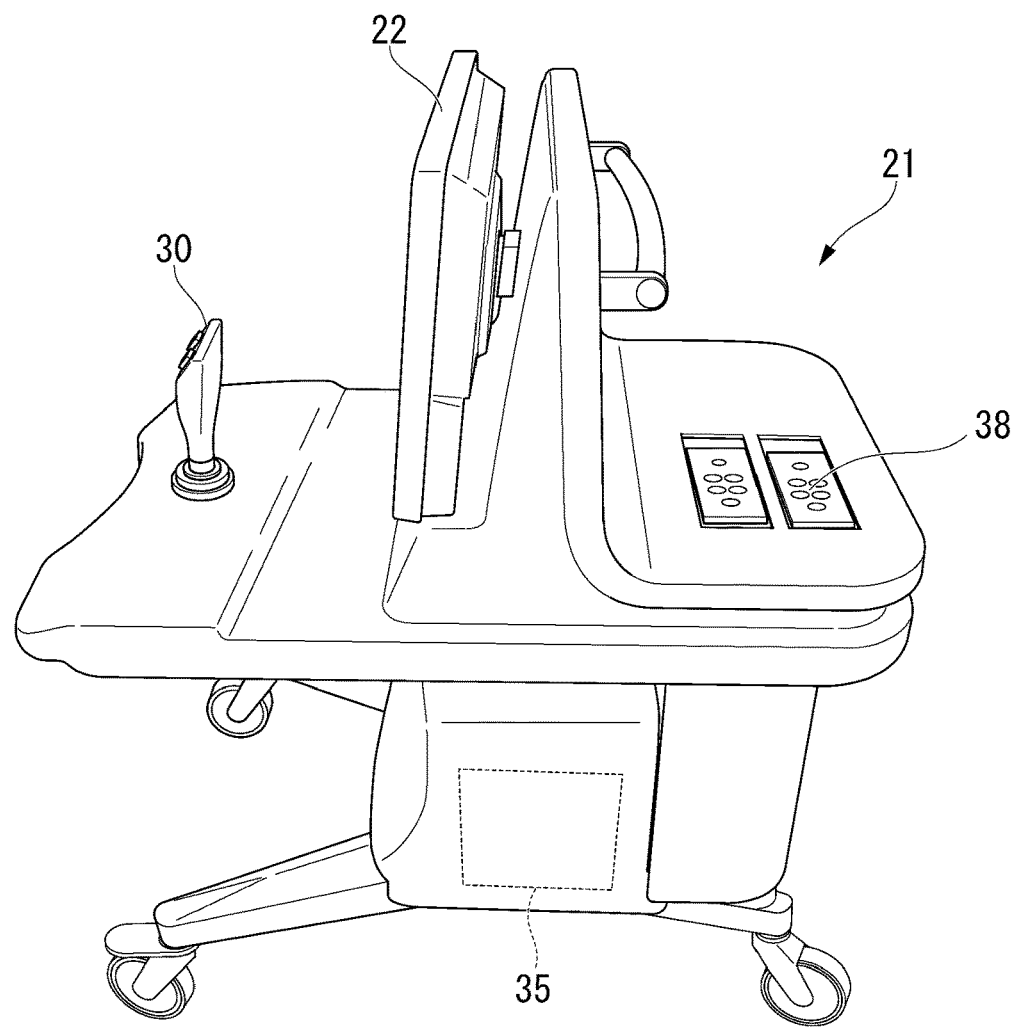
FIG. 3 is a view showing a console of the medical system.

FIG. 3 is a view showing the console 21.

The console 21 includes an operation device 30 that is operated and input by the operator Op, a controller 35 that operates the treatment tool unit 40 based on an output from the operation device 30, a motor unit 38 on which the treatment tool unit 40 is mounted, and a monitor (display part) 22.

Figure 4:
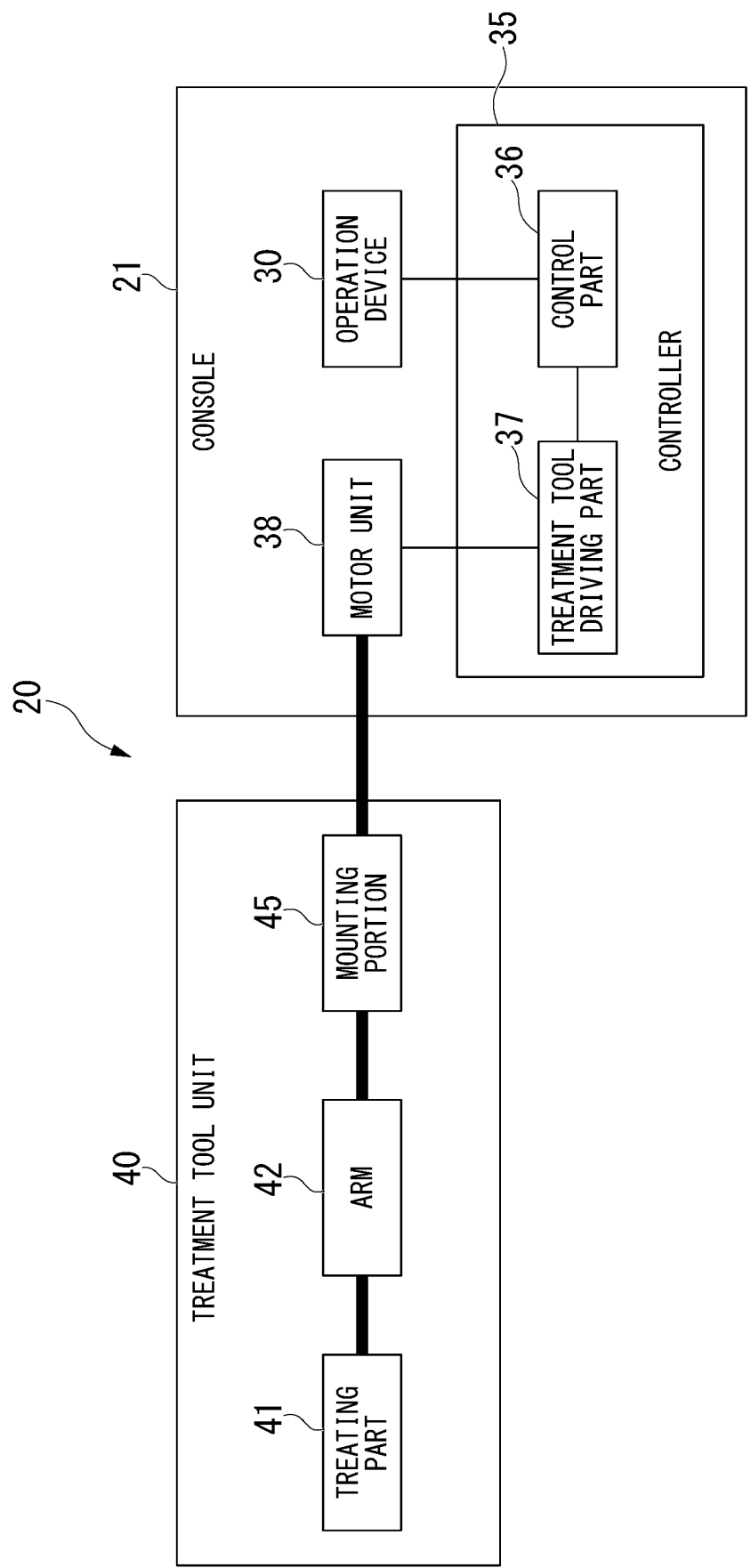
FIG. 4 is a functional block diagram of a manipulator of the medical system.

FIG. 4 is a functional block diagram of the manipulator 20 in a state where the treatment tool unit 40 is mounted on the console 21. In FIG. 4, the monitor 22 is omitted. In FIG. 4, a thick line connecting components represents a physical coupling capable of transmitting power, and a thin line connecting components represents a logical coupling capable of transmitting and receiving signals.

Figure 5:
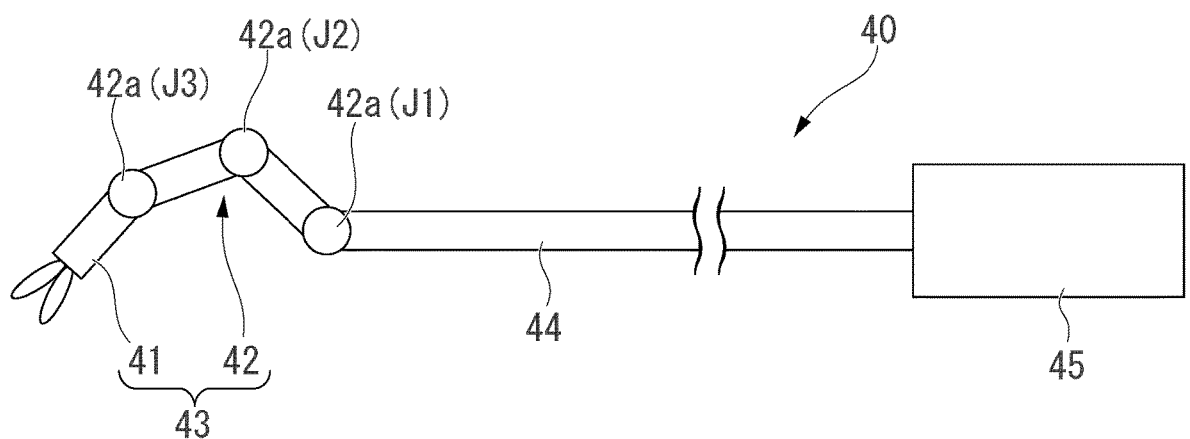
FIG. 5 is a view schematically showing a treatment tool unit of the medical system.

FIG. 5 is a view schematically showing the treatment tool unit 40.

The treatment tool unit 40 includes an arm portion 43 and a mounting portion 45. A region between the arm portion 43 and the mounting portion 45 is a flexible connecting portion 44 having flexibility.

The arm portion 43 includes a treating part (moving part) 41 provided at the distal end, and an arm 42 on which the treating part 41 is mounted.

The mounting portion 45 is detachable from the motor unit 38 and is mounted on the motor unit 38 to transmit the drive of the motor unit 38 to drive the treating part 41 and the arm 42.

The treating part (moving part) 41 is an apparatus that performs medical treatment such as the grasping forceps 49 and the electric knife 48. The treatment tool unit 40 shown in FIG. 5 is equipped with the grasping forceps 49 as the treating part 41. A distal end of an operation wire for opening and closing the grasping forceps 49 is mounted on the grasping forceps 49. The operation wire is inserted through the inside of the treatment tool unit 40, and the proximal end of the operation wire is mounted on the mounting portion 45.

The arm 42 has a plurality of joints (moving parts) 42a (J3, J2, J1). Each joint 42a is connected to a plurality of pulleys provided inside the mounting portion 45 via transmission members. As shown in FIG. 5, the joint 42a (J3), the joint 42a (J2), and the joint 42a (J1) are arranged from the distal end side closest to the treating part 41 toward the proximal end side.

The pulley is connected to the output shaft of the motor unit 38 so as to rotate by the operation of the motor unit 38. The rotation shaft of the pulley is supported by the mounting portion 45. The transmission member is wound around the pulley. When the pulley rotates, the transmission member moves forward and backward so that the joints 42a are driven.

Figure 6:
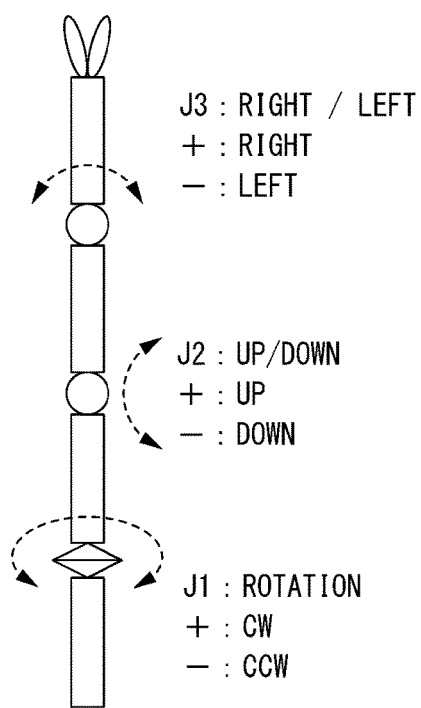
FIG. 6 is a view showing an operation direction of a joint of the treatment tool unit of the medical system.

FIG. 6 is a view showing the movable directions of the joints 42a.

The joint 42a (J1) is a joint that rotates around the longitudinal axis of the arm 42 as shown in FIG. 6.

The joint 42a (J2) is a joint that bends the arm 42 as shown in FIG. 6.

The joint 42a (J3) is a joint that bends the arm 42 as shown in FIG. 6, and the bending direction is orthogonal to the direction in which the joint 42a (J2) bends the arm 42.

The treatment tool unit 40 has treatment tool identification information (slave identification information). The treatment tool identification information is, for example, a treatment tool number from which the type of the treatment tool unit 40 can be determined. In addition to the treatment tool number, various types of information can be included in the treatment tool identification information. For example, the treatment tool identification information may include a serial number or the like from which an individual tool can be identified even if the same type of treatment tool unit 40 is used. Moreover, information of the configuration of the moving part such as a joint may be included.

The treatment tool identification information is stored in a memory of an electric circuit provided in the treatment tool unit 40. The treatment tool unit 40 can transmit treatment tool identification information by communication via the electric circuit or wireless communication.

Further, the treatment tool identification information may be a mechanical structure provided in a portion where the treatment tool unit 40 and the console 21 are mounted. The console 21 on which the treatment tool unit 40 is mounted can determine the type of the treatment tool unit 40 according to the mechanical structure.

Figure 7:
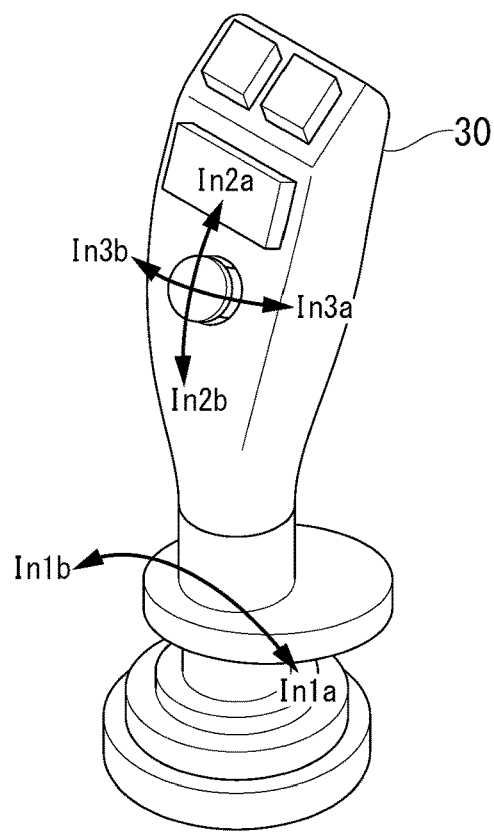
FIG. 7 is a view showing an operation device of a console of the medical system.

FIG. 7 is a view showing the operation device 30 of the console 21.

The operation device 30 is a device that receives an operation input by the treatment tool unit 40 that is detachable from the console 21. In the present embodiment, the operation device 30 is a joystick as shown in FIG. 7, and can be appropriately selected from various known configurations in consideration of performance, use, or the like. The operation device 30 can receive three types of inputs, that is, input 1 (In1), input 2 (In2), and input 3 (In3). Each input can receive an input amount in the plus direction (In1a, In2a, In3a) and the minus direction (In1b, In2b, In3b) from a reference position.

Figure 8:
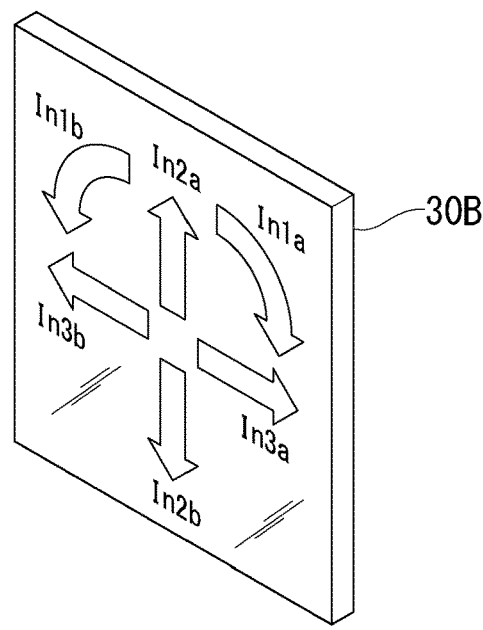
FIG. 8 is a view showing a modification of the operation device of the console of the medical system.

The operation device 30 is not limited to a joystick as shown in FIG. 7. For example, as shown in FIG. 8, an operation device 30B that is a modification of the operation device 30 is configured with a touch panel. Similarly to the operation device 30, the operation device 30B can receive three types of inputs, that is, input 1 (In1), input 2 (In2), and input 3 (In3). Each input can receive an input amount in the plus direction (In1a, In2a, In3a) and the minus direction (In1b, In2b, In3b) from the reference position.

The operation device 30 may be provided with a treatment operation part (operation part) for operating the treating part (operation part) 41. The specific mode of the treatment operation part can be appropriately set according to the configuration of the treating part 41 or the like. For example, when the treating part 41 is the grasping forceps 49, a structure having a button for opening and closing the grasping forceps 49 may be used. When the treating part 41 is the electric knife 48 that is energized to be used, a structure having a button for switching energization on and off may be used.

The console 21 can be used with the operation device 30 selected from various operation devices. It is also possible to mount a plurality of operation devices on the console at the same time and use them in combination.

The treatment operation part (operation part) may be a switch such as a foot switch provided separately from the operation device 30 or the like. The operator Op operates the treating part 41 and the joints 42a (moving part) of the treatment tool unit 40 by combining the operation device 30 and the switch or the like.

The operation device 30 has operation device identification information. The operation device identification information is, for example, an operation device number from which the type of the operation device 30 can be determined. In addition to the operation device number, various types of information can be included in the operation device identification information. For example, a serial number or the like from which an individual device can be identified even in the same type of operation device 30 may be included in the operation device identification information. Moreover, information of the configuration of the operation part may be included.

The operation device identification information is stored in the memory of the electric circuit provided in the operation device 30. The operation device 30 can transmit the operation device identification information by communication via the electric circuit or wireless communication.

The operation device identification information may be a mechanical structure provided in a portion where the operation device 30 and the console 21 are mounted. The console 21 on which the operation device 30 is mounted can determine the type of the operation device 30 from the mechanical structure.

The monitor 22 is a device that displays an image acquired by the endoscope 10. The monitor 22 is configured by a known display device such as an LCD display.

The motor unit 38 is physically coupled to the arm portion 43 via the mounting portion 45. The motor unit 38 has a plurality of drive sources such as a motor, and each joint 42a of the arm 42 is connected to the corresponding drive source via a pulley of the mounting portion 45 and a transmission member.

The controller 35 is a device that controls the manipulator 20, and includes a control part 36 and a treatment tool driving part 37 as shown in FIG. 4.

The control part 36 controls the manipulator 20 and the like. The control part 36 is configured by a device (computer) including hardware processor capable of executing a program such as a central processing unit (CPU) and a memory. The function of the control part 36 can be realized as a software function by the control part 36 reading and executing a program for controlling the CPU.

Note that some or all of the functions of the control part 36 may not be realized as software functions, but may be configured by a dedicated logic circuit or the like.

Figures 9, 10:
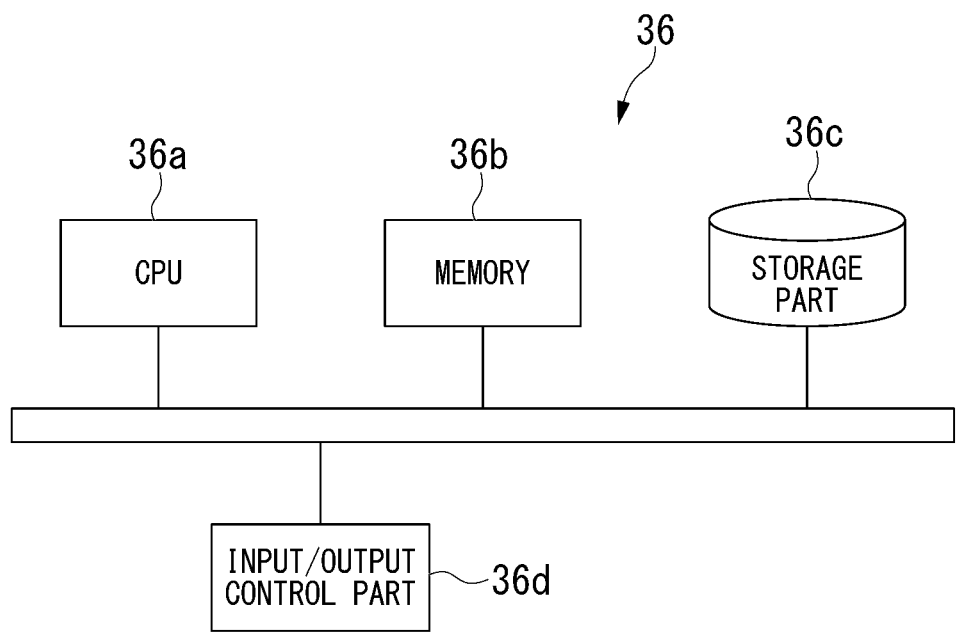
FIG. 9 is a view showing an example of the overall configuration of a control part of the medical system.
FIG. 10 is a view showing an example of a conversion table generated by the control part of the medical system.

FIG. 9 is a view showing an example of the overall configuration of the control part 36.

As shown in FIG. 9, the control part 36 includes a CPU 36a, a memory 36b that can read a program, a storage part 36c, and an input/output control part 36d. A program provided to the control part 36 for controlling the operation of the controller 35 is read into the memory 36b and executed by the CPU 36a.

The storage part 36c is a non-volatile recording medium that stores the above-described program and necessary data. The storage part 36c is configured by, for example, a ROM or a hard disk. The program recorded in the storage part 36c is read into the memory 36b and executed by the CPU 36a.

The input/output control part 36d receives input data from the operation device 30, the treatment tool unit 40, and the like, and transmits the input data to a module such as the CPU 36a inside the control part 36. Further, the input/output control part 36d generates a control signal or the like for the treatment tool driving part 37 or the like, based on an instruction from the CPU 36a, when the CPU 36a controls the treatment tool driving part 37 or the like.

The control part 36 described above is not limited to a device provided in one piece of hardware. For example, the control part 36 may be configured by separating the CPU 36a, the memory 36b, the storage part 36c, and the input/output control part 36d as separate hardware and connecting the hardware with a communication line. Alternatively, the control part 36 may achieve a cloud system by separating the storage part 36c and similarly connecting it with a communication line.

The treatment tool driving part 37 controls the motor unit 38 according to the output of the control part 36 to drive the treatment tool unit 40.

The treatment tool driving part 37 can drive each joint 42a of the arm 42 by driving a driving source such as a motor provided in the motor unit 38 and rotating a pulley supported by the mounting portion 45.

In addition, the treatment tool driving part 37 controls the treating part 41. For example, when the electric knife 48 is mounted as the treating part 41, it is possible to control whether electricity is supplied to the electric knife 48. When the grasping forceps 49 is mounted as the treating part 41, the opening/closing operation of the grasping forceps 49 can be controlled.

The control part 36 can read the treatment tool identification information from the treatment tool unit 40 mounted on the console 21 via the electric circuit. When the controller 35 further has a wireless communication function, the treatment tool identification information may be read from the treatment tool unit 40 by wireless communication.

The storage part 36c stores a treatment tool database from which information such as the configuration of the moving part of the treatment tool can be extracted from the treatment tool number included in the treatment tool identification information. In the treatment tool database, the treatment tool number of the treatment tool unit 40 that can be mounted on the console 21 and the configuration of the moving part of the treatment tool are stored in advance. The treatment tool database can be updated at any time.

The control part 36 can read the operation device identification information from the operation device 30 mounted on the console 21 via the electric circuit. When the controller 35 further has a wireless communication function, the treatment tool identification information may be read from the operation device 30 by wireless communication.

The storage part 36c stores an operation device database from which information such as the configuration of the operation part of the operation device 30 can be extracted from the operation device number included in the operation device identification information. In the operation device database, the operation device number of the operation device 30 that can be mounted on the console 21 and the configuration of the operation part of the operation device 30 are stored in advance. The operation device database can be updated at any time.

The control part 36 can acquire user identification information from an input device such as a keyboard provided separately from the operation device 30. The user identification information is, for example, a user number from which an operator can be identified. The operator and the user number are associated with each other in advance. The control part 36 acquires the user number by allowing the operator to input the user number from an input device such as a keyboard. Further, the control part 36 may acquire the user number from the ID card held by the operator by wireless communication or the like.

The storage part 36c stores a conversion table that associates the operation part of the treatment tool unit 40 with the operation part of the operation device 30. The conversion table is newly generated under the control of the medical system 100 described below. The newly generated conversion table is stored in the storage part 36c together with user identification information, treatment tool identification information, and operation device identification information, as a conversion table history. The conversion table corresponding to the operator Op is stored in the storage part 36c.

FIG. 10 is a view showing the conversion table corresponding to the treatment tool number "S01" and the operation device number "M01" of the operator "UesrA". The conversion table shows the correspondence between the input (In1a, In2a, In3a, In1b, In2b, In3b) of the operation part of the operation device 30 and the moving parts (J1, J2, J3) of the treatment tool unit 40. The numbers in the conversion table represent the ratio (gain) of the operation amount of the operation part to the input amount of the operation part. When the number is "2", the operation amount is doubled when the input amount is the same as compared with the case where the number is "1". A negative number indicates that the moving part operates in the opposite direction as compared with a positive number.

Figure 11:
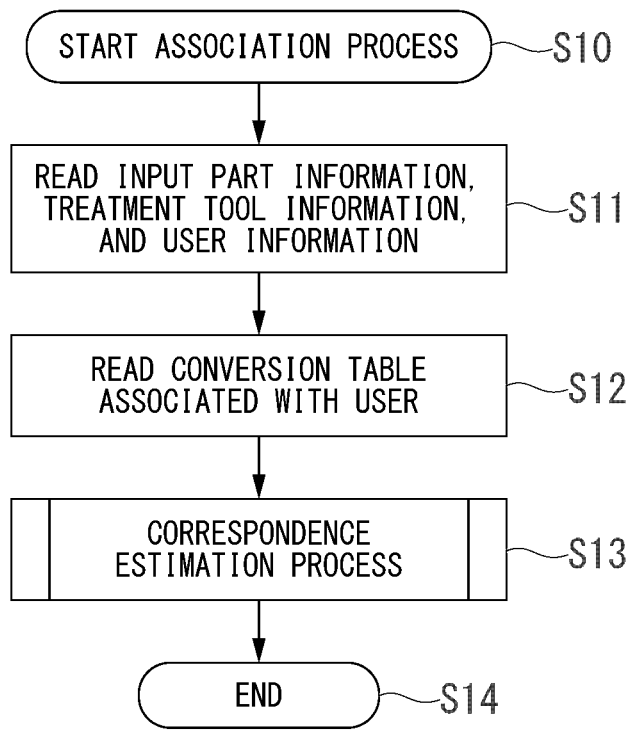
FIG. 11 is an association process by the control part of the medical system.
Figure 12:
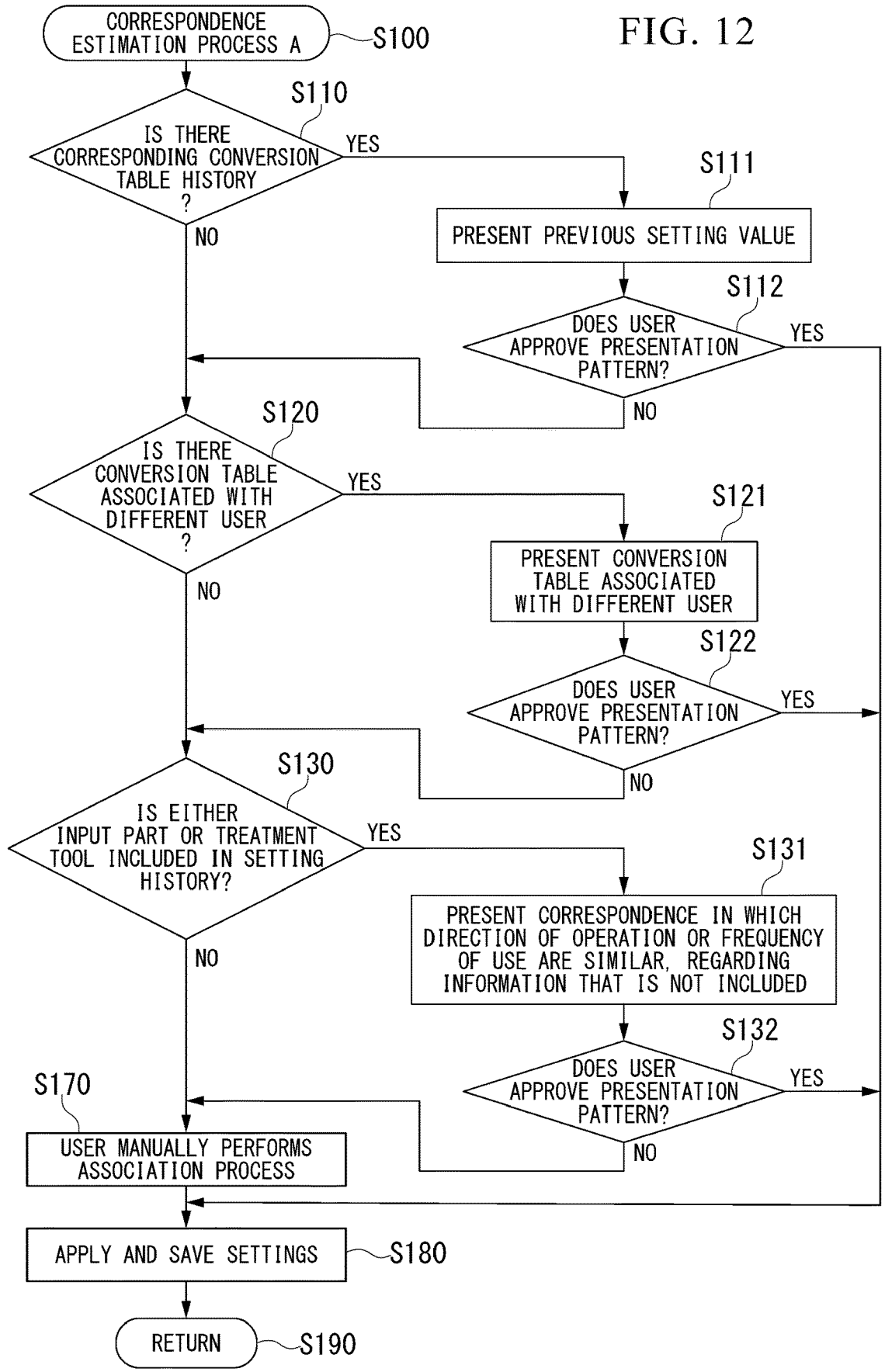
FIG. 12 is a flowchart of control of correspondence estimation process A by the control part of the medical system.

The operation of the medical system 100 configured as described above and the operation method of the medical system 100 will be described with reference to FIGS. 11 to 13. FIG. 11 is a flowchart of control of the control part 36. FIG. 12 is a flowchart of control of "correspondence estimation process A" which is a subroutine in the flowchart of control of the control part 36 shown in FIG. 11.

As shown in FIG. 1, the medical system 100 is operated by at least two persons, that is, an operator Op who operates the console 21 and a scopist Sc who operates the overtube 80 and the endoscope 10.

The operator Op selects the treatment tool unit 40 and the operation device 30 that are optimal for the treatment. The selected operation device 30 is mounted on the console 21. As shown in FIG. 2, when two treatment tool units 40 are used, the operation devices 30 corresponding to the respective treatment tool units 40 are mounted on the console 21.

As shown in FIG. 1, the scopist Sc inserts the endoscope 10 into the first lumen 81 of the overtube 80. Further, the scopist Sc inserts the treatment tool unit 40 into the second lumen 82 of the overtube 80.

The scopist Sc inserts the overtube 80 into which the endoscope 10 and the treatment tool unit 40 are inserted into the anus of the patient P. Subsequently, the scopist Sc advances the overtube 80 in the large intestine while observing the image acquired by the endoscope 10 and introduces the overtube 80 through which the endoscope 10 is inserted to the vicinity of the target portion.

Subsequently, the scopist Sc causes the endoscope 10 to protrude from the overtube 80, performs a bending operation as necessary, and secures a visual field when performing treatment on the target portion. This completes the preparation process.

After completing the preparation process, the mounting portion 45 of the treatment tool unit 40 is mounted on the motor unit 38 of the console 21. Hereinafter, the description will follow the flowchart of control of the "association process" of the control part 36 shown in FIG. 11.

As shown in FIG. 11, when the treatment tool unit 40 and the operation device 30 are mounted, the control part 36 starts control of the "association process" (step S10). Until the association is completed, the control part 36 invalidates the operation input of the operation device 30, and the scopist cannot operate the treatment device unit 40 by operating the operation device 30.

Next, the control part 36 performs step S11.

In step S11, as shown in FIG. 11, the control part 36 acquires the treatment tool identification information of the mounted treatment tool unit 40 and the operation device identification information of the mounted operation device 30, by communication via the electric circuit or wireless communication.

In addition, the control part 36 displays a message prompting the operator to input the user identification information from the input device on the monitor 22, and acquires the user identification information input by the operator from the input device. The user identification information may be acquired from an ID card held by the operator by wireless communication or the like.

Next, the control part 36 performs step S12.

In step S12, as shown in FIG. 11, the control part 36 reads the conversion table history for the treatment tool unit 40 and the operation device 30 to be used, corresponding to the operator Op, based on the user identification information, the treatment tool identification information, and the operation device identification information, from the storage part 36c.

Next, the control part 36 performs step S13.

In step S13, as shown in FIG. 11, the control part 36 performs a "correspondence estimation process A" which is a subroutine. Hereinafter, the description will follow the flowchart of control of the control part 36 shown in FIG. 12.

In step S100, as shown in FIG. 12, the control part 36 starts the control of the correspondence estimation process A. Next, the control part 36 performs step S110.

In step S110, as shown in FIG. 12, the control part 36 determines whether the conversion table corresponding to the operator Op has been read from the storage part 36c in step S12. When the operator Op has used the combination of the treatment tool unit 40 and the operation device 30 that have been previously mounted in the medical system 100, the used conversion table is stored in the storage part 36c as a conversion table history. The conversion table history is specified as a proposed conversion table. In this case, the control part 36 next performs step S111.

When the corresponding conversion table does not exist in the storage part 36c, the control part 36 next performs step S120.

In step S111, as shown in FIG. 12, the control part 36 proposes to the operator Op the conversion table specified in step S110 (conversion table proposal process). Proposals to the operator are made by displaying the conversion table on the monitor 22 as shown in FIG. 10. In addition, the control part 36 causes the monitor 22 to display a message that prompts the operator to input the approval of the operator Op for the proposed conversion table from the input device.

Next, the control part 36 performs step S112.

In the conversion table shown in FIG. 10, input 1 (In1) is associated with the joint 42a (J1), input 2 (In2) is associated with the joint 42a (J2), and input 3 (In3) is associated with the joint 42a (J3).

In step S112, as shown in FIG. 12, when the control part 36 approves the conversion table proposed by the operator Op, the control part 36 next performs step S180. When the table is not approved, the control part 36 next performs step S120.

In step S120, as shown in FIG. 12, a conversion table corresponding to another user is read from the storage part 36c, and it is determined whether there is a conversion table history corresponding to the combination of the mounted treatment tool unit 40 and the mounted operation device 30. When there is a corresponding conversion table history, the control part 36 next performs step S121. When there is no corresponding conversion table history, the control part 36 next performs step S130.

In step S121, as shown in FIG. 12, the control part 36 proposes to the operator Op the conversion table specified in step S110. The proposal to the operator Op is the same as in step S112.

Figures 13, 14, 15:
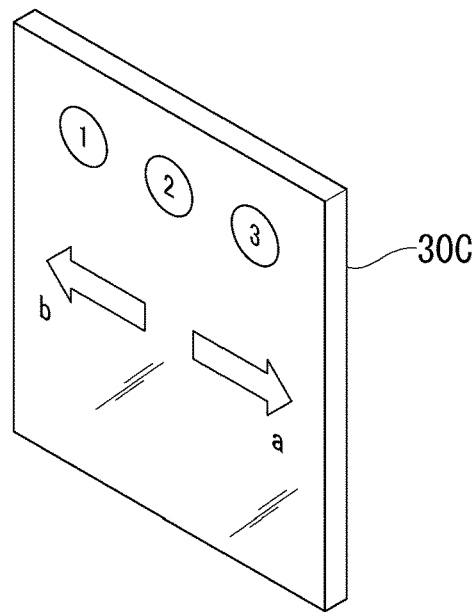
FIG. 13 is a view showing an example of the conversion table generated by the control part of the medical system.
FIG. 14 is a view showing a modification of the operation device of the medical system.
FIG. 15 is a view showing an example of the conversion table generated by the control part of the medical system.

For example, when the conversion table of another user "UserB" shown in FIG. 13 is in the storage part 36c, this is proposed to the operator Op (UserA). In the conversion table shown in FIG. 13, input 1 (In1) is associated with the joint 42a (J1), input 2 (In2) is associated with the joint 42a (J3), and input 3 (In3) is associated with the joint 42a (J2).

Next, the control part 36 performs step S122.

In step S122, as shown in FIG. 12, when the operator Op approves the proposed conversion table, the control part 36 next performs step S180. When the table is not approved, the control part 36 next performs step S130.

In step S130, as shown in FIG. 12, the control part 36 determines whether there is a conversion table history including one of the mounted treatment tool unit 40 or the mounted operation device 30 in the storage part 36c. In this case, the conversion table history may correspond to the operator Op, or may correspond to another user. When there is a conversion table history including either one, the control part 36 next performs step S131. When there is no conversion table history including either one, the control part 36 next performs step S170.

In step S131, as shown in FIG. 12, the control part 36 specifies the conversion table with reference to the conversion table history including another treatment tool unit 40 or the operation device 30 having a similar configuration (number of degrees of freedom, operation direction) of the operation part or the moving part and a similar usage frequency, among the conversion table history including either the mounted treatment tool unit 40 or the mounted operation device 30.

The control part 36 proposes the specified conversion table to the operator Op. The proposal to the operator Op is the same as in step S112.

Next, the control part 36 performs step S132.

In step S132, as shown in FIG. 12, when the control part 36 approves the conversion table proposed by the operator Op, the control part 36 next performs step S180. When the table is not approved, the control part 36 next performs step S170.

In step S170, as shown in FIG. 12, since there is no conversion table that can be proposed, the control part 36 displays a message on the monitor 22 prompting to input the conversion table from the input device, and acquires the conversion table input from the input device by the operator Op.

Next, the control part 36 performs step S180.

In step S180, as shown in FIG. 12, the control part 36 sets a conversion table approved or input by the operator Op as the conversion table, to be used for associating the moving part of the treatment tool unit 40 with the operation part of the operation device 30. In addition, the control part 36 stores the conversion table approved or input by the operator Op in the storage part 36c as the conversion table history together with the user identification information, the treatment tool identification information, and the operation device identification information (conversion table storage process).

Next, the control part 36 performs step S190.

In step S190, as shown in FIG. 12, the control part 36 ends the control of "correspondence estimation process A", and then performs step S14 shown in FIG. 11 to end the "association process".

After completing the "association process", the operator Op can perform a desired treatment on the target portion by appropriately operating the operation device 30 while confirming the video of the target portion displayed on the monitor 22. The operator Op operates the operation device 30 and the scopist Sc operates the endoscope 10, so as to move the treating part 41 and the endoscope 10 to a place where the target portion can be treated.

(Effects of the First Embodiment)

According to the medical system 100 of the present embodiment, the user identification information of the user (operator Op) of the treatment tool unit 40, the treatment tool identification information of the treatment tool unit 40, and the operation device identification information of the operation device 30 are acquired, and a corresponding conversion table can be generated and proposed. The treatment tool unit 40 and the operation device 30 can be easily associated with each other.

According to the medical system 100 of the present embodiment, the conversion table used last by the operator Op can be proposed from the corresponding conversion table history. Even when there is no corresponding conversion table history, a conversion table can be proposed by referring to a conversion table history corresponding to another user, or another treatment tool unit 40 or operation device 30 with a similar configuration or usage frequency. By using the conversion table history, the treatment tool unit 40 and the operation device 30 can be easily associated with each other.

(Modification)

The first embodiment of the present invention has been described in detail with reference to the drawings. However, the specific configuration is not limited to this embodiment, and design changes and the like within the scope of the present invention are included. In addition, the constituent elements shown in the above-described first embodiment and the modifications shown below can be combined as appropriate.

For example, in the above-described embodiment, the number of joints 42a (moving parts) of the treatment tool unit 40 and the number of operation parts of the operation device 30 coincide. However, the aspect of the joints 42a (operation parts) of the treatment tool unit 40 and the operation part of the operation device 30 is not limited to this. For example, an operation device 30C that is a modification of the operation device 30 shown in FIG. 14 has three push buttons and two direction buttons. FIG. 15 is a conversion table associating the treatment tool unit 40 with the operation device 30C. The operator Op can operate the joint 42a (J1) by operating the direction button while pressing the push button 1. Even when the number of joints 42a (operation parts) of the treatment tool unit 40 and the number of operation parts of the operation device 30 do not coincide, the medical system 100 can perform association using the conversion table.

For example, the flowchart of control shown in the above embodiment may be one in which the flow order is appropriately changed. Moreover, the flowchart of control shown in the above embodiment may be changed in part.

Second Embodiment

A second embodiment of the present invention will be described with reference to FIG. 16. This embodiment is different from the first embodiment in that an operation history is stored. In the following description, components that are the same as those already described are assigned the same reference numerals and redundant description is omitted.

The overall configuration of the medical system 200 according to the present embodiment is the same as that of the medical system 100 according to the first embodiment. The control part 36 of the medical system 200 is different in that the operation history of the operation device 30 of the operator Op is stored together with the user identification information, the treatment tool identification information, and the operation device identification information.

The operation history stored by the control part 36 includes, for example, the number of uses of the joint 42a (operation part) of the treatment tool unit 40 and the operation part of the operation device 30, and the operation input tendency. The operation input tendency is, for example, the number of operations consecutively operated by the same operation part or the types of operation parts operated simultaneously. Additional information such as the type of procedure and the portion to be treated may be stored together. These operation histories are stored for each operator Op (operation history storage process).

Further, the medical system 200 controls the correspondence estimation process B, which is partly different from the correspondence estimation process A of the medical system 100.

Hereinafter, flow of control of the control part 36 will be described with reference to FIG. 16. FIG. 16 is a flowchart of control of the correspondence estimation process B by the control part 36. The flowchart of control shown in FIG. 16 differs from the flowchart of control shown in FIG. 10 only in that it further includes step S113, step S114, and step S115. Since the other steps are the same, the description thereof is omitted.

Figure 16:
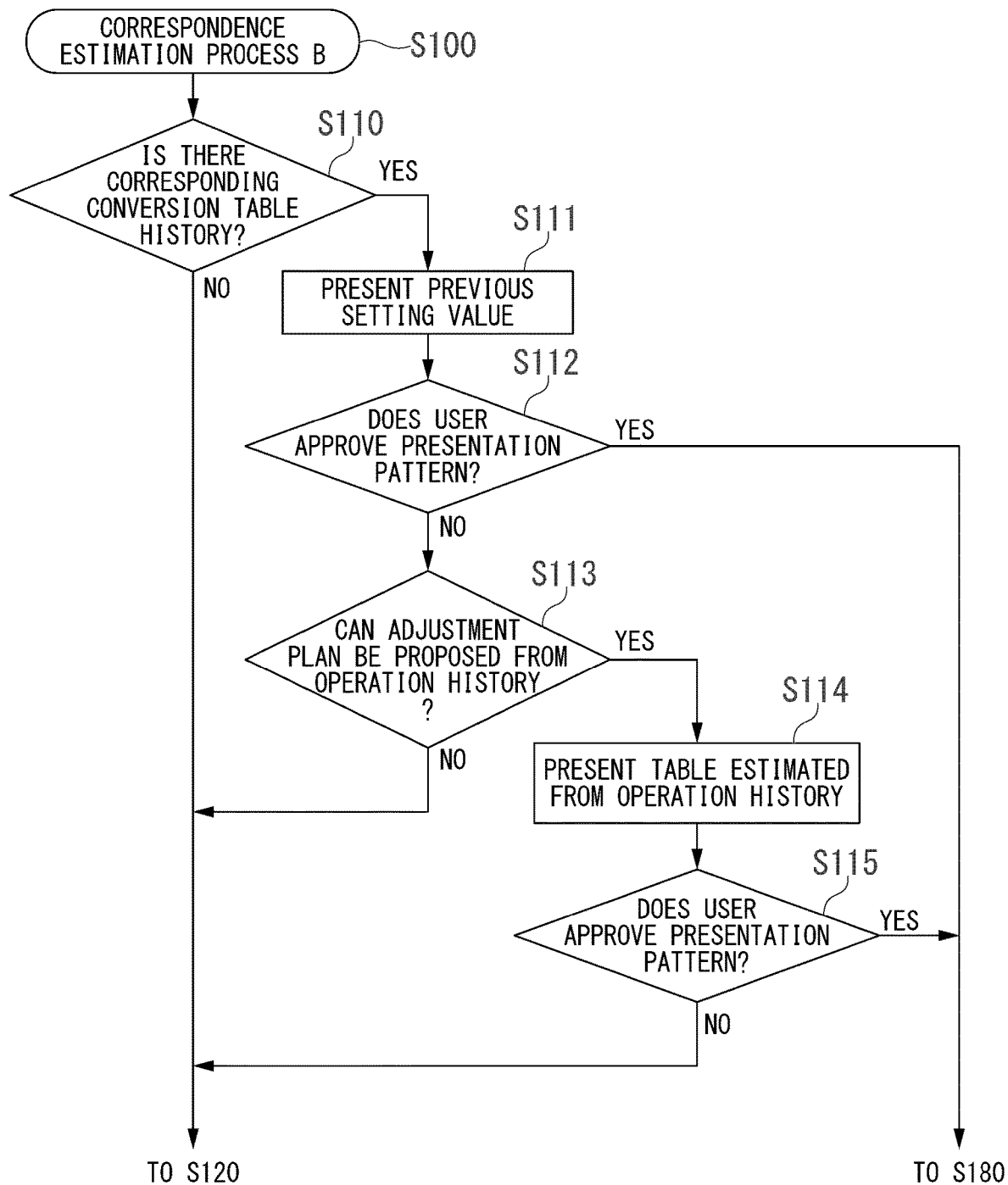
FIG. 16 is a flowchart of control of a correspondence estimation process B by the control part of the medical system according to a second embodiment of the present invention.

In step S112, as shown in FIG. 16, when the control part 36 does not approve the conversion table proposed by the operator Op, the control part 36 next performs step S113.

In step S113, as shown in FIG. 16, the control part 36 determines whether an adjustment plan of the conversion table can be proposed from the stored operation history. Based on the user identification information, the treatment tool identification information, and the operation device identification information, the control part 36 reads out, from the storage part 36c, the operation history of the operated operator Op about the treatment tool unit 40 and the operation device 30 to be used.

In step S110, the control part 36 has already read out the conversion table history for the treatment tool unit 40 and the operation device 30 to be used corresponding to the operator Op from the storage part 36c, to specify the conversion table history as the conversion table to be proposed. In step S113, as shown in FIG. 16, the control part 36 estimates and generates the adjustment plan of the conversion table based on the conversion table.

For example, the control part 36 generates the adjustment plan of the conversion table as follows.

When there is a bias in the number of operations consecutively operated by the same operation part, the adjustment plan is generated so that the bias is reduced. The operation part that is operated consecutively is considered to have a small amount of operation output corresponding to the operation part. Therefore, the gain is adjusted to increase the operation amount of the operation output corresponding to the operation part. When there is an operation part that is used less frequently, the operation by the moving part corresponding to the operation part may be changed to a different operation. The bias in the number of operations can be reduced, and the operator Op can use the operation part efficiently.

Furthermore, the control part 36 may generate the adjustment plan of the conversion table so that the total number of operations of the operation device 30 is reduced. For example, when the operation history includes many operations in which the operations A and B are continuously operated, a new operation input that performs the operations A and B simultaneously or continuously may be assigned to the operation part. Since the total number of operations of the operation device 30 is reduced, the operator Op can use the operation part more efficiently.

In step S113, as shown in FIG. 16, when it is determined that the adjustment plan of the conversion table can be proposed, the control part 36 next performs step S114. When it is determined that the proposal cannot be made, the control part 36 next performs step S120.

In step S114, as shown in FIG. 16, the control part 36 proposes to the operator Op the conversion table to be proposed that has been specified in step S113. The proposal to the operator Op is made by displaying the conversion table on the monitor 22. In addition, the control part 36 causes the monitor 22 to display a message that prompts the operator to input the approval of the operator Op for the proposed conversion table from the input device.

Next, the control part 36 performs step S115.

In step S115, as shown in FIG. 16, when the operator Op approves the proposed conversion table, the control part 36 next performs step S180. When the table is not approved, the control part 36 next performs step S120.

(Effect of the Second Embodiment)

According to the medical system 200 of the present embodiment, it is possible to propose the adjustment plan of the conversion table based on the conversion table used last by the operator Op, from the corresponding operation history. By estimating and generating a new conversion table so that the deviation of the number of operations in the plurality of operation parts is reduced or the total number of operations is reduced, the association between the treatment tool unit 40 and the operation device 30 can be easily performed and the operator Op can use the operation part more efficiently.

(Modification)

The second embodiment of the present invention has been described in detail with reference to the drawings. However, the specific configuration is not limited to this embodiment, and design changes and the like within a scope not departing from the gist of the present invention are included. In addition, the constituent elements shown in the above-described second embodiment and the modified examples described below can be configured in appropriate combinations.

For example, in the above-described embodiment, the conversion table is proposed based on the type of the treatment tool unit 40, but the proposal aspect is not limited to this. For example, when the treatment tool identification information includes a manufacturing number or the like from which an individual unit can be identified even in the same type of treatment tool unit 40, the number of repeated uses of the moving part may be acquired from the operation history for each individual part, and an adjustment plan considering estimation of deterioration due to repeated use may be generated. For example, for an moving part having a large number of repeated uses, it may be assumed that the operation wire or the like has deteriorated, and the gain of the moving part may be set small in order to prevent damage to the operation wire or the like.

Third Embodiment

A third embodiment of the present invention will be described with reference to FIG. 17. This embodiment is different from the first embodiment and the second embodiment in that the correspondence estimation process is performed not only when the treatment tool unit 40 or the like is mounted, but also during the treatment. In the following description, components that are the same as those already described are assigned the same reference numerals and redundant description is omitted.

The overall configuration of the medical system 300 according to the present embodiment is the same as that of the medical system 100 according to the first embodiment. After completing the "association process", the operator Op can perform a desired treatment on the target portion by appropriately operating the operation device 30 while confirming the video of the target portion displayed on the monitor 22. Hereinafter, the description will follow the flowchart of control of an "in-treatment association process" by the control part 36 shown in FIG. 17.

In step S200, as shown in FIG. 16, the control part 36 starts control of the "in-treatment association process". The control part 36 initializes a counter that counts a time (non-operation time) for which there is no operation input from the operation device 30. Next, the control part 36 performs step S210.

Figure 17:
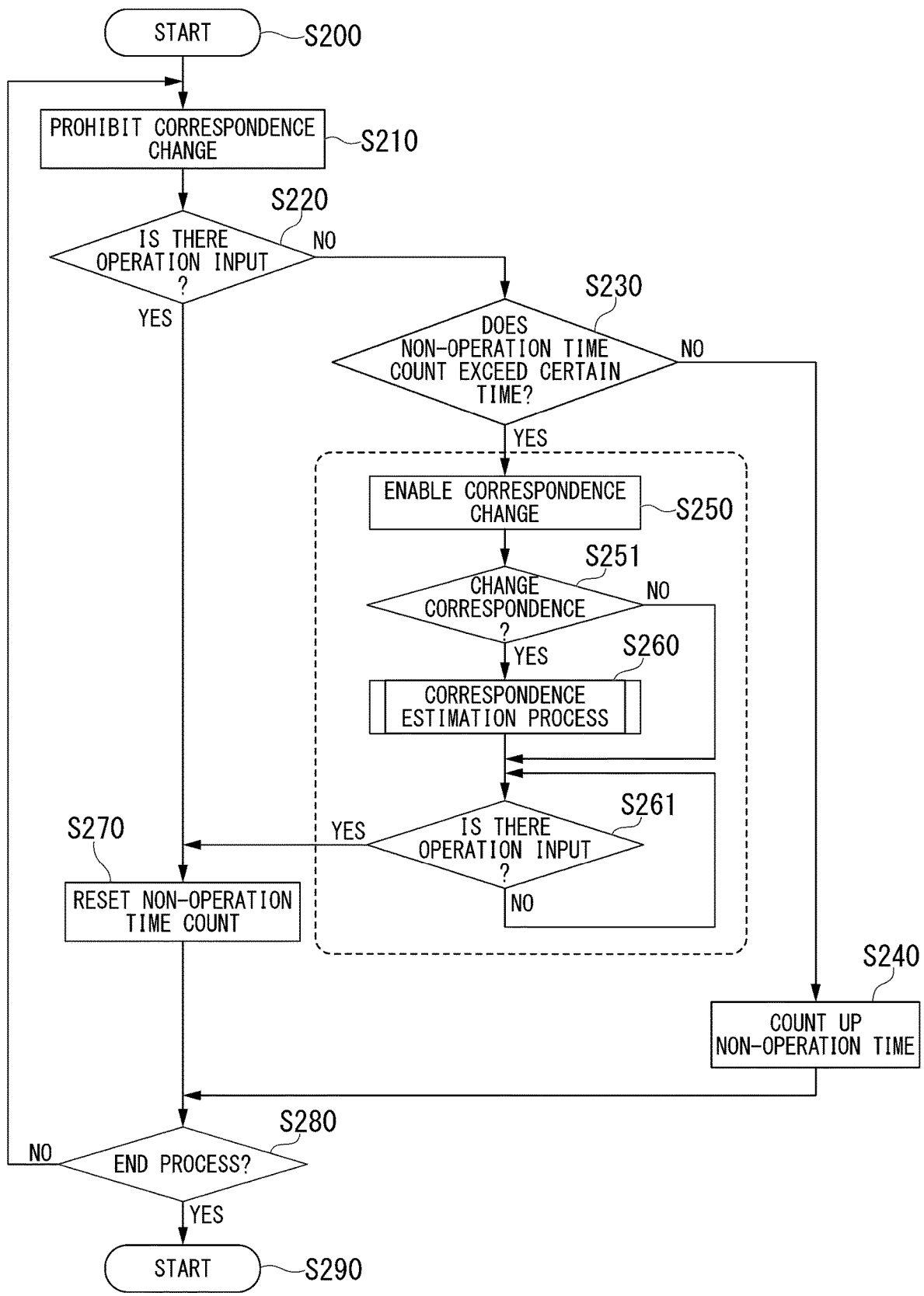
FIG. 17 is a flowchart of control of an in-treatment association process by the control part of the medical system according to a third embodiment of the present invention.

In step S210, as shown in FIG. 17, the control part 36 prohibits changing the correspondence. It is possible to prevent an unexpected operation from occurring due to a change of the correspondence during the treatment. Next, the control part 36 performs step S220.

In step S220, as shown in FIG. 17, the control part 36 determines whether or not there is an operation input from the operation device 30. When there is an operation input, the control part 36 next performs step S270. When there is no operation input, the control part 36 next performs step S230.

In step S230, as shown in FIG. 17, the control part 36 determines whether the non-operation time counted by the counter exceeds a certain time. When the predetermined time is exceeded, the control part 36 next performs step S250. When the predetermined time is not exceeded, the control part 36 next performs step S240.

In step S240, as shown in FIG. 17, the control part 36 counts up a counter of the non-operation time. Next, the control part 36 performs step S280.

In step S250, as shown in FIG. 17, the control part 36 determines that the non-operation time exceeds a certain time and the treatment is not interrupted even when the association process is performed, and validates the change of the correspondence. Thereby, the correspondence can be changed. Here, the operation input of the operation device 30 may be invalidated.

Next, the control part 36 performs step S251.

In step S251, as shown in FIG. 17, the control part 36 displays a message for inquiring whether or not changing of the correspondence is desired, and acquires the intention of changing the correspondence of the operator Op input by the operator Op from the input device. When the operator Op desires to change the correspondence, the control part 36 next performs step S260. When the operator Op does not desire to change the correspondence, the control part 36 next performs step S261.

In step S260, as shown in FIG. 17, the control part 36 performs a "correspondence estimation process". The "correspondence estimation process" is the same process as that described as the correspondence estimation process A of the first embodiment or the correspondence estimation process B of the second embodiment. The conversion table is updated by the "correspondence estimation process". Even when the "correspondence estimation process" is performed, there is a case in which the conversion table is not updated. Next, the control part 36 performs step S261.

In step S261, as shown in FIG. 17, the control part 36 waits for an operation input from the operation device 30.

When the operation input of the operation device 30 has been invalidated, the operation input of the operation device 30 is validated at this time.

When there is an operation input from the operation device 30, the control part 36 next performs step S270.

In step S270, as shown in FIG. 17, the control part 36 resets a counter that counts non-operation time. Next, the control part 36 performs step S280.

In step S280, as shown in FIG. 17, the control part 36 confirms whether or not the operator Op ends the treatment. When the operator Op ends the treatment, the control part 36 next performs step S290 and ends the control of the "in-treatment association process". When the operator Op does not end the treatment, the control part 36 next performs step S210.

(Effect of the Third Embodiment)

According to the medical system 300 of the present embodiment, when the period in which there is no operation input to the operation device 30 exceeds a predetermined period, by generating and proposing a conversion table again, the operator Op can select and change the conversion table according to the treatment status during the treatment. Further, by limiting the proposal of the conversion table only when the period in which there is no operation input to the operation device 30 exceeds a predetermined period, the conversion table can be prohibited from being changed during the operation of the operation device 30. Therefore, it is possible to prevent an unexpected motion caused by simultaneous operation input and conversion table change.

Fourth Embodiment

A fourth embodiment of the present invention will be described with reference to FIGS. 18 and 19. This embodiment is different from the third embodiment in the "correspondence estimation process" in the control of the "in-treatment association process". In the following description, components that are the same as those already described are assigned the same reference numerals and redundant description is omitted.

The overall configuration of the medical system 400 according to the present embodiment is the same as the medical system 300 according to the third embodiment. Similarly to the medical system 300 according to the third embodiment, the control part 36 of the medical system 400 controls the "in-treatment association process" shown in FIG. 17. The control part 36 performs the correspondence estimation process C in the "in-treatment association process". Hereinafter, the description will follow the flowchart of control of the correspondence estimation process C of the control part 36 shown in FIG. 18.

When the non-operation time exceeds a certain time during the treatment and the change of the correspondence is validated, the control part 36 starts the control of the correspondence estimation process C (step S300). Next, the control part 36 performs step S310.

Figures 18, 19:
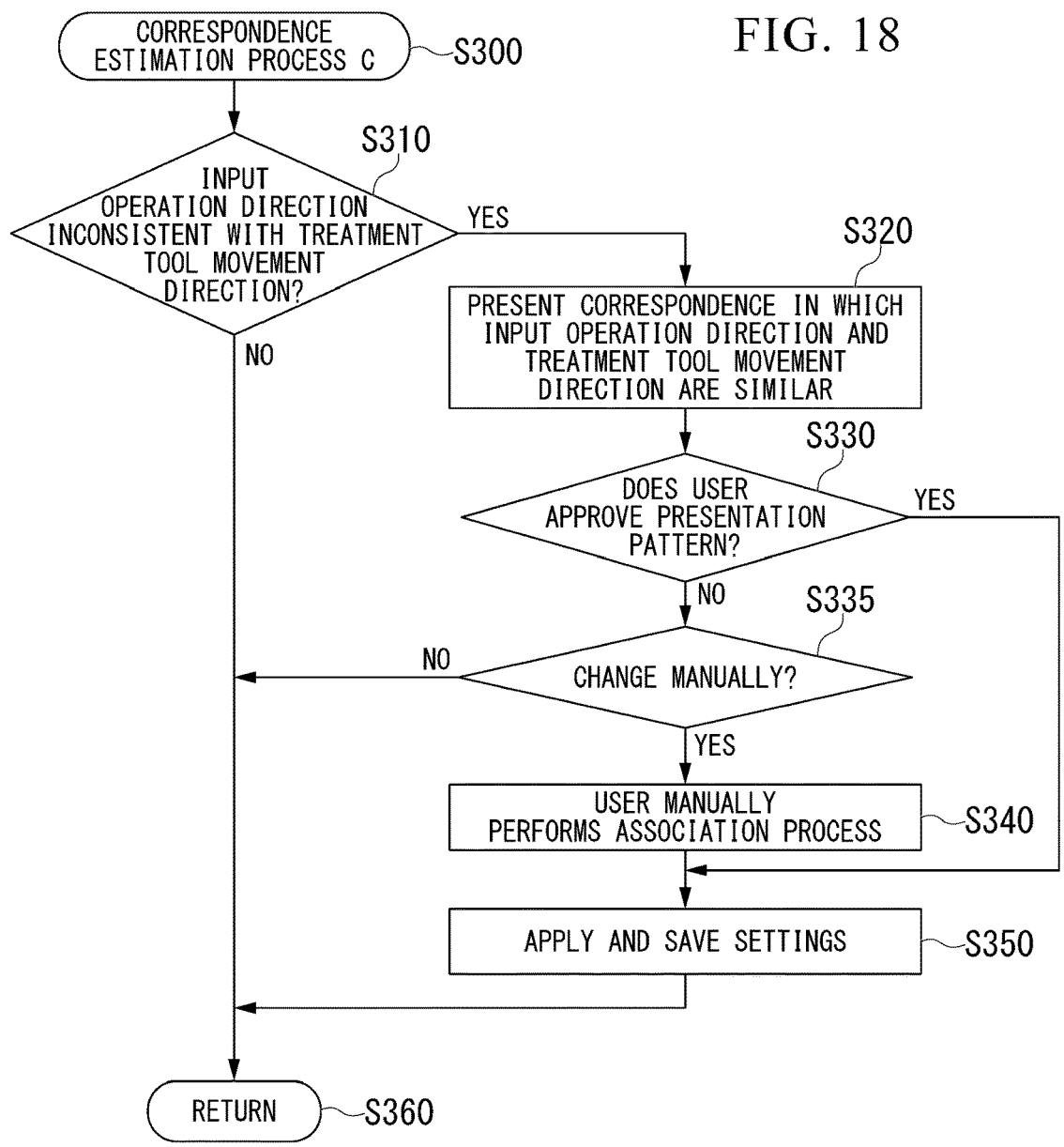
FIG. 18 is a flowchart of control of correspondence estimation process C by the control part of the medical system according to a fourth embodiment of the present invention.
FIG. 19 is a view showing an example of a conversion table generated by the control part of the medical system.

In step S310, as shown in FIG. 18, the control part 36 determines whether or not the input operation direction of the treatment tool unit 40 in the visual field of the endoscope 10 needs to coincide with the operation direction of the operation device 30. When the relative position between the endoscope 10 and the treatment tool unit 40 is changed, the relationship between the input operation direction of the treatment tool unit 40 and the operation direction of the operation device 30 in the visual field of the endoscope 10 may be different from when the "association process" is performed. In this case, the control part 36 determines that the input operation direction of the treatment tool unit 40 in the visual field of the endoscope 10 needs to coincide with the operation direction of the operation device 30, and then performs step S320.

When the relationship between the input operation direction of the treatment tool unit 40 and the operation direction of the operation device 30 in the visual field of the endoscope 10 coincide as compared with the case when the "association process" was performed most recently, step S360 is performed.

The relative position between the endoscope 10 and the treatment tool unit 40 may be determined by image processing of a captured image of the endoscope 10. For calculating the relative position, control information of the treatment tool unit 40, information on a sensor incorporated in the treatment tool unit 40, or the like may be used.

In step S320, as shown in FIG. 18, the control part 36 proposes a conversion table in which the relationship between the input operation direction of the treatment tool unit 40 and the operation direction of the operation device 30 in the field of view of the endoscope 10 correspond as compared with the case when the "association process" was performed most recently.

It is assumed that the field of view of the endoscope 10 is rotated 90 degrees with respect to the treatment tool unit 40 as compared with the case when the "association process" was most recently performed. Further, it is assumed that the conversion table is set to the conversion table shown in FIG. 10 by the "association process" performed most recently. In step S320, the control part 36 exchanges the operation parts (In2, In3) corresponding to the joint 42a (J2) and the joint 42a (J3) as in the conversion table shown in FIG. 19. The joint 42a (J2) and the joint 42a (J3) are joints whose bending directions are orthogonal to each other. When the field of view of the endoscope 10 is rotated 90 degrees, by replacing the operation parts corresponding to the joint 42a (J2) and the joint 42a (J3), the operator Op can obtain a feeling of operation similar to the feeling of operation of the treatment instrument unit 40 by the "association process" performed most recently.

In step S330, as shown in FIG. 18, when the control part 36 approves the conversion table proposed by the operator Op, the control part 36 next performs step S350. When the table is not approved, the control part 36 next performs step S335.

In step S335, as shown in FIG. 18, the control part 36 displays a message inquiring whether the operator Op desires to manually change the conversion table, and acquires the will of manual change of the operator Op input by the operator Op from the input device. When the operator Op desires manual change, the control part 36 next performs step S340. When the operator Op does not desire manual change, the control part 36 next performs step S360.

Step S340 is the same as step S170, step S350 is the same as step S180, and step S360 is the same as step S190.

(Effect of the Fourth Embodiment)

According to the medical system 400 of the present embodiment, for example, when the field of view of the endoscope 10 changes 90 degrees during treatment, a conversion table that matches the input operation directions of up, down, left and right of the treatment instrument unit with the operation direction of the operation device 30 is proposed. That is, by referring to the relative positional relationship between the endoscope 10 and the treatment tool unit 40 and generating a conversion table to propose, the feeling of operation of the treatment tool unit 40 by the operation device 30 can be maintained even when the field of view of the endoscope 10 is changed. The operator Op can intuitively operate the treatment tool unit 40 even when the field of view of the endoscope 10 changes.

Fifth Embodiment

A fifth embodiment of the present invention will be described with reference to FIGS. 20 and 21. The present embodiment is different from the first embodiment to the fourth embodiment in that an "association display process" is performed together with the "association process" and "in-treatment association process". In the following description, components that are the same as those already described are assigned the same reference numerals and redundant description is omitted.

The overall configuration of the medical system 500 according to the present embodiment is the same as that of the medical system 100 according to the first embodiment. Similarly to the medical system 100 according to the first embodiment and the medical system 300 according to the third embodiment, the control part 36 of the medical system 500 performs control of an "association process" and an "in-treatment association process" shown in FIG. 17 and the like. In parallel with these processes, the control part 36 performs an "association display process". Hereinafter, the description will follow a flowchart of control of "association display process" of the control part 36 shown in FIG. 20.

Figure 20:
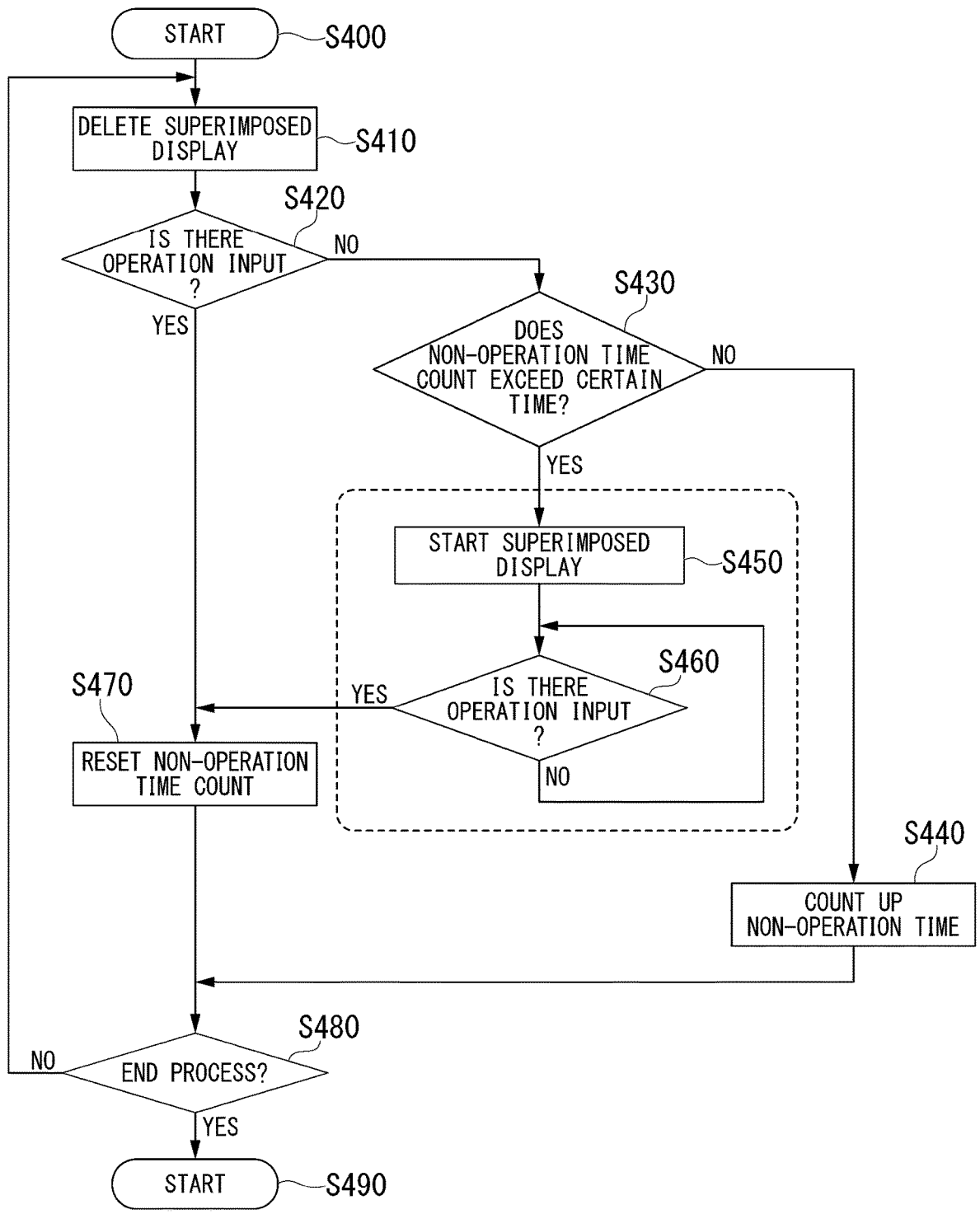
FIG. 20 is a flowchart of control of an association display process by the control part of the medical system according to a fifth embodiment of the present invention.

After completion of the "association process", as shown in FIG. 20, the control part 36 starts the control of the "association display process" (step S400). The control part 36 initializes a counter that counts a time when there is no operation input from the operation device 30 (non-operation time). Next, the control part 36 performs step S410.

In step S410, as shown in FIG. 20, when the association display displayed in the "association display process" is displayed superimposed on the monitor 22, the control part 36 deletes the association display. Next, the control part 36 performs step S420.

In step S420, as shown in FIG. 20, the control part 36 determines whether there is an operation input from the operation device 30. When there is an operation input, the control part 36 next performs step S470. When there is no operation input, the control part 36 next performs step S430.

In step S430, as shown in FIG. 20, the control part 36 determines whether the non-operation time counted by the counter has exceeded a certain time. When the predetermined time is exceeded, the control part 36 next performs step S450. When the predetermined time is not exceeded, the control part 36 next performs step S440.

The fixed time used in step S430 may be different from the fixed time used in step S230.

In step S440, as shown in FIG. 20, the control part 36 counts up a counter for non-operation time. Next, the control part 36 performs step S480.

Figure 21:
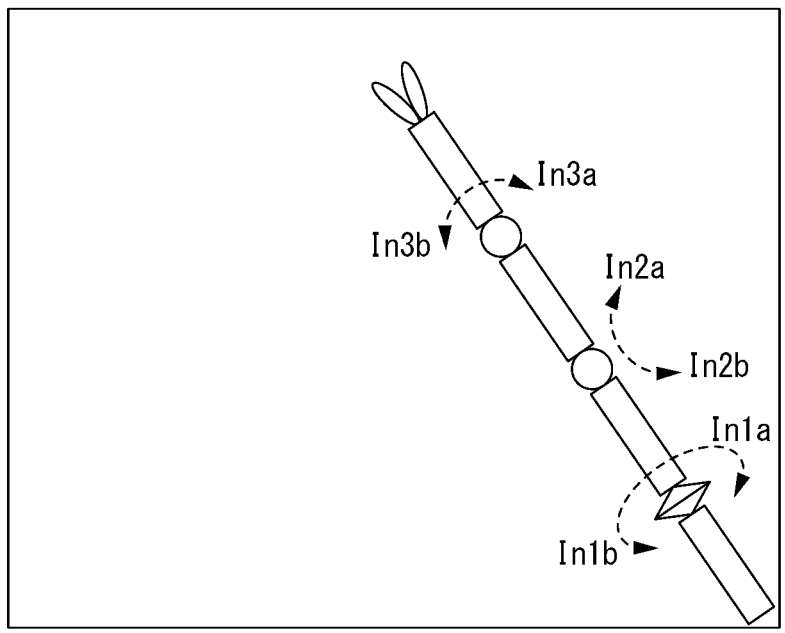
FIG. 21 is a view showing an association display generated by the control part of the medical system.

In step S450, as shown in FIG. 20, the control part 36 acquires the correspondence between the current operation part and the moving part from the conversion table, and superimposes and displays the identification display of the operation part corresponding to the moving part of the treatment tool unit 40 imaged by the endoscope 10 at the position where the moving part is imaged, as shown in FIG. 21 (association display process). Next, the control part 36 performs step S460.

In step S460, as shown in FIG. 20, the control part 36 waits for an operation input from the operation device 30. When there is an operation input from the operation device 30, the control part 36 next performs step S480.

Step S480 is the same as step S280, and step S490 is the same as step S290.

During the period in which the "association display process" described in the present embodiment is being executed, the "in-treatment association process" described in the third embodiment and the fourth embodiment may be performed in parallel.

(Effect of the Fifth Embodiment)

According to the medical system 500 of the present embodiment, the identification display of the operation part corresponding to the moving part of the treatment tool unit 40 imaged by the endoscope 10 is superimposed and displayed at the position where the moving part is imaged. Thus, the operator Op can confirm the correspondence between the moving part and the operation part, and can prevent the recognition error of the correspondence. In addition, since the superimposed display is performed only while the operation by the operator Op is interrupted, the operator Op can concentrate on the procedure during the operation input.

Sixth Embodiment

Figure 22:
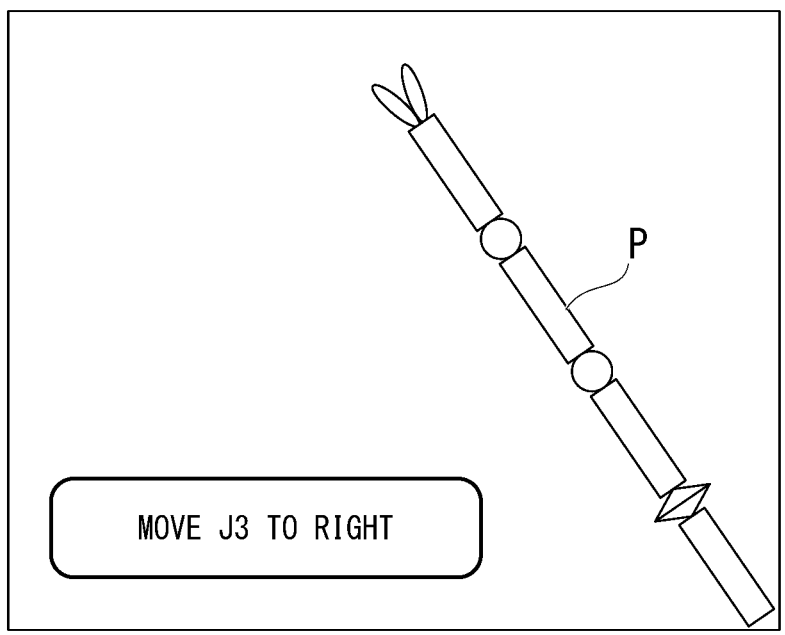
FIG. 22 is a view showing an interactive display by the medical system according to a sixth embodiment of the present invention.
Figure 23:
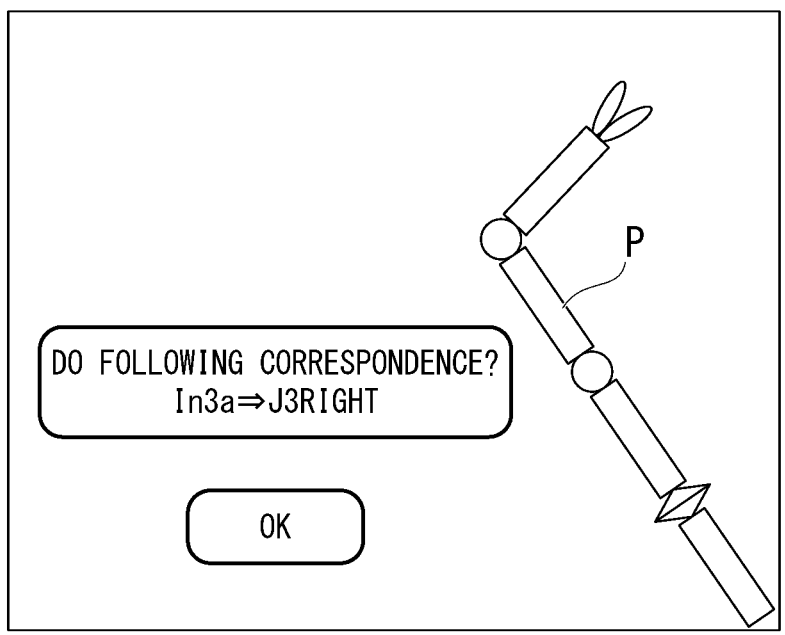
FIG. 23 is a view showing the interactive display of the medical system.

A sixth embodiment of the present invention will be described with reference to FIGS. 22 and 23. In the present embodiment, the "interactive display process" is performed when "the user manually performs association" in the "association process" or "in-treatment association process" from the first embodiment to the fifth embodiment.

The overall configuration of the medical system 600 according to the present embodiment is the same as the medical system 100 according to the first embodiment. In step S170 in the correspondence estimation process A of the first embodiment and in step S340 in the correspondence estimation process C of the fourth embodiment, the control part 36 does not have a conversion table that can be proposed, and a message prompting the user to input the conversion table from the input device is displayed on the monitor 22. At this time, as shown in FIG. 22, the control part 36 displays a pseudo image P of the treatment tool unit 40 having the same configuration as the mounted treatment tool unit 40, on the screen of the monitor 22.

Further, one moving part is selected from the moving parts to be manually set, and one piece of operation content is selected from the operation content of the moving part. Further, a message prompting the user to operate the operation part of the operation device 30 is displayed on the screen of the monitor 22 so that the selected moving part performs the operation of the selected operation content. In FIG. 22, "joint 42a (J3)" is selected as the moving part, and "right" is selected from the operation content of the joint 42a (J3).

The operator Op selects and inputs the operation part that moves the "joint 42a (J3)" to the "right". It is assumed that the operator Op selects the input In3a as the operation part. As shown in FIG. 23, the control part 36 displays the pseudo image P with the joint 42a (J3) bent to the right on the monitor 22 (interactive display step). After confirming the operation of the pseudo image P, the operator Op uses the input device or the like to determine whether to approve the association between the input In3a and the joint 42a (J3).

(Effects of the Sixth Embodiment)

According to the medical system 600 of the present embodiment, the pseudo image P of the treatment tool unit 40 that operates based on the generated conversion table is displayed on the monitor 22 and interactive conversion table input can be performed. Thereby, the burden of manual setting of the conversion table of the operator Op can be reduced. Further, by displaying the pseudo image P on the monitor 22, manual setting can be performed intuitively, and manual setting errors can be reduced.

What is claimed is:

1. A medical system, comprising:
a slave having at least one moving part;
an operation device having at least one operation part; and
a processor that controls operations of the slave based on a conversion table that associates operations of the moving part of the slave with inputs of the operation part of the operation device,
wherein the processor is programmed to execute:
acquiring user identification information of a user of the slave, slave identification information of the slave, and operation device identification information of the operation device, and
generating and proposing the conversion table based on the user identification information, the slave identification information, and the operation device identification information.

2. The medical system according to claim 1, wherein the processor is programmed to execute:
causing a memory to store the conversion table used by the user as a conversion table history together with the user identification information, the slave identification information, and the operation device identification information,
when there is the conversion table history corresponding to the user identification information, the slave identification information, and the operation device identification information, proposing the corresponding conversion table history as a conversion table, and
when there is no conversion table history corresponding to the user identification information, the slave identification information, and the operation device identification information, generating and proposing the conversion table by referring to the conversion table history.

3. The medical system according to claim 1, wherein the processor is programmed to execute:
causing a memory to store an operation history of the operation device operated by the user together with the user identification information, the slave identification information, and the operation device identification information, and
generating and proposing the conversion table based on the operation history, so that a deviation in the number of operations in a plurality of operation parts is reduced or a total number of the operations is reduced.

4. The medical system according to claim 1, wherein, the processor is programmed to execute:
when a period in which there is no operation input to the operation device exceeds a predetermined period, generating and proposing the conversion table again.

5. The medical system according to claim 1, further comprising an endoscope,
wherein the processor is programmed to execute:
generating and proposing the conversion table referring to a relative positional relationship between the endoscope and the slave.

6. The medical system according to claim 1, further comprising:
an endoscope; and a display part configured to display an image captured by the endoscope,
    wherein the processor is programmed to execute:
        when a period in which there is no operation input to the operation device exceeds a predetermined period, causing the display part to display the image which superimposes an identification display of the operation part corresponding to the moving part of the imaged slave, on a position where the moving part is imaged.

7. The medical system according to claim 1, further comprising a display part configured to display an image,
    wherein the processor is programmed to execute:
        when the conversion table is generated and proposed, causing the display part to display a pseudo image of the slave that operates based on the generated conversion table.

8. A medical system operation method, comprising:
    a conversion table storage process in which a conversion table associating an moving part of a slave with an operation part of an operation device that receives an operation of the slave is stored, together with user identification information of a user of the slave, slave identification information of the slave, and operation device identification information of the operation device, as a conversion table history; and
    a conversion table proposing process in which the conversion table is generated and proposed with reference to the conversion table history.

9. The medical system operation method according to claim 8, further comprising:
    an operation history storage process in which an operation history of the operation device operated by the user is stored together with the user identification information, the slave identification information, and the operation device identification information,
    wherein, in the conversion table proposing process, the conversion table is proposed and generated based on the operation history, so that a deviation of the number of operations in a plurality of operation parts is reduced or a total number of the operations is reduced.

10. The medical system operation method according to claim 8, wherein,
    in the conversion table proposing process, the conversion table is generated and proposed again when a period in which there is no operation input to the operation device exceeds a predetermined period.

11. The medical system operation method according to claim 8, wherein,
    in the conversion table proposing process, a relative positional relationship between the endoscope and the slave is referred to, to generate and propose the conversion table.

12. The medical system operation method according to claim 8, further comprising:
    an association display process in which, when a period in which there is no operation input to the operation device exceeds a predetermined period, an identification display of the operation part corresponding to the moving part of the slave imaged by the endoscope is superimposed on a position where the moving part is imaged.

13. The medical system operation method according to claim 8, further comprising:
    an interactive display process in which a pseudo image of the slave that operates based on the generated conversion table is displayed on a display part when the conversion table is generated and proposed.

* * * * *